United States Patent [19]
Abramov et al.

[11] Patent Number: 5,492,115
[45] Date of Patent: Feb. 20, 1996

[54] RESUSCITATION BREATHING APPARATUS

[76] Inventors: Vladimir V. Abramov, 124 Prospect Mira, Block 14, Apartment 40, Moscow, Russian Federation; Juriy V. Novikov, 22 "G" Kirov Street, Apartment 10, Ljubertsi, Moscow Region, Russian Federation

[21] Appl. No.: 163,826

[22] Filed: Dec. 8, 1993

[51] Int. Cl.[6] .................................................. A61H 31/00
[52] U.S. Cl. .............................. 128/205.24; 128/207.16; 601/41
[58] Field of Search .................... 601/41, 43, 44; 128/202.28, 202.29, 203.11, 204.18, 204.26, 205.24, 205.25, 207.16

[56] References Cited

U.S. PATENT DOCUMENTS

| | | | |
|---|---|---|---|
| 2,436,853 | 3/1948 | Coleman . | |
| 2,699,163 | 1/1955 | Engstrom . | |
| 3,385,295 | 5/1968 | Beasley | 128/205.24 |
| 3,503,393 | 3/1970 | Manley | 128/204.26 |
| 3,683,655 | 8/1972 | White et al. | 601/44 |
| 3,802,417 | 4/1974 | Lang | 601/44 |
| 4,121,579 | 10/1978 | Bird | 128/204.26 |
| 4,211,221 | 7/1980 | Schwanbom et al. | 128/204.26 |
| 4,397,306 | 9/1983 | Weisfeldt et al. . | |
| 4,424,806 | 1/1984 | Newman et al. . | |
| 4,481,944 | 11/1984 | Bunnell | 128/204.18 |
| 4,770,170 | 9/1988 | Sato et al. | 128/205.24 |
| 4,813,409 | 3/1989 | Ismach | 128/205.24 |
| 4,840,167 | 6/1989 | Olsson et al. . | |
| 4,883,051 | 11/1989 | Westenskow et al. | 128/204.21 |
| 4,945,899 | 8/1990 | Sugiyama et al. . | |
| 5,040,529 | 8/1991 | Zalkin | 128/204.18 |
| 5,230,330 | 7/1993 | Price | 128/203.11 |
| 5,360,000 | 11/1994 | Carter | 128/205.24 |

FOREIGN PATENT DOCUMENTS

| | | | |
|---|---|---|---|
| 1069814A | 1/1984 | U.S.S.R. . | |
| 1558404 | 4/1990 | U.S.S.R. | 601/41 |
| 3000062 | 1/1993 | WIPO | 601/41 |

*Primary Examiner*—Richard J. Apley
*Assistant Examiner*—Jeanne M. Clark
*Attorney, Agent, or Firm*—Harold L. Jackson

[57] ABSTRACT

A resuscitation breathing apparatus includes a high pressure source of breathable gas and an inhalation chamber having an inlet and an outlet. A face mask is connected to the outlet of the inhalation chamber. Inhalation and exhalation check valves in the face mask allow air to enter and exit a patient's lungs. An inhalation valve, connected between the inhalation chamber and the high pressure source, is controlled to open and close the inhalation valve when the pressure reaches first and second values, respectively. The inhalation chamber is vented to lower the pressure within the chamber after the inhalation valve is closed. The apparatus further includes a chest compressor in the form of an inflatable cuff for applying pressure to the patient's lungs during the exhalation phase. The cuff is inflated by gas from the high pressure source when the inhalation valve is closed.

22 Claims, 3 Drawing Sheets

RESUSCITATION BREATHING APPARATUS

BACKGROUND OF THE INVENTION

1. Field of the Invention

This invention relates to apparatus for improving or restoring the breathing functions of a user or patient.

2. Description of the Prior Art

A need to improve or restore the breathing functions of an individual are commonly encountered. For example, a person's (hereinafter "patient") pulmonary or breathing functions may become impaired (e.g., due to an asthma attack) or totally or partially disabled due to an accident etc. Respiratory devices are available which implement the forced ventilation of a patient's lungs based on "passive" or "active" expiration.

Respirators which are based on passive expiration typically include a source of pressurized gas containing oxygen, a face mask or an airway device and electrically controlled valves for alternatively connecting the face mask to the gas source and to the atmosphere so that the lungs are alternately inflated and deflated.

To provide active expiration, mechanical pressure may be applied on the chest or on the patient's abdomen, for example, by means of a person's hands to force air out of the lungs or the lungs may be subjected to a reduced pressure, for example, by means of a vacuum pump, to such air out of the lungs. Only trained specialists should attempt to exert mechanical pressure with his or her hands to force ventilate a patient's lungs. Inadvertent pressure on the chest or abdomen during expiration or exhalation may lead to an excessive pressure in the lungs of the patient. In addition, such a forced ventilation method can be practiced only for relatively short time periods in critical situations. Such a method is not applicable for prolonged forced ventilation of the lungs, for example, in the case of asthma or a paralysis of the breathing organs.

Subjecting the lungs to a reduced or a sub-atmospheric pressure to force air out of the lungs is not possible in all circumstances and again cannot be used for prolonged periods. Moreover, such a procedure may be dangerous with respect to certain lung diseases, which are accompanied by the loss of elasticity of the bronchi.

Bronchial walls which have become weak and flabby due to certain diseases may collapse in response to the application of a sub-atmospheric pressure to the patient's mouth leading to the well known "air entrapment" thereby increasing the effect of expiratory closing of the breathing path.

Various types of prior art apparatus for assisting or reproducing the pulmonary and/or cardiac functions of a patient are disclosed in the patent literature. See, for example, U.S. Pat. No. 2,436,853 which issued to E. D. Coleman on Mar. 2, 1948. The Coleman apparatus includes a face mask, an inflatable chest belt and a high pressure source of gas connected to the mask for supplying breathable gas under pressure to the face mask during inhalation and for supplying the same (or different) gas to the chest belt during the exhalation phase. The Coleman apparatus poses several problems. First, the patient's exhaled gas is not limited to the face mask (which does not contain inlet and outlet check valves) but must flow through an extended exhaust tube 12 and valve 14 (open only when supply valve 16 is closed). As a result a considerable volume of expired or exhaled air containing $CO_2$ can be rebreathed by the patient. In addition, sterilization of the Coleman apparatus would be extremely difficult since the expired air is not confined to the face mask. The Coleman mechanical linkage would also be affected by gravity (rendering the orientation of the apparatus important) and subject to wear (resulting in changes in performance characteristics with use). Last, the design of the Coleman apparatus would not be compatible with portability.

Also see, U.S. Pat. No. 4,424,806 (complex electronically controlled inflatable vest and valve mechanism for feeding gas containing oxygen to an airway coupled to the patient's lungs); U.S. Pat. No. 4,945,899 (a rigid shell jacket for surrounding the patient's chest and an electronic control system for alternatively connecting the interior of the jacket to a vacuum source or to atmosphere); U.S. Pat. No. 4,397,306 (electronically controlled chest compressor and lung ventilation means); U.S. Pat. No. 4,840,167 (an electronically controlled chest compressor and ventilator for promoting blood circulation); U.S. Pat. No. 2,699,163 (a mechanical respirator with motor driven pistons for supplying air under pressure to an inflatable vest and for controlling the supply of air to a patient's lungs); U.S. Pat. No. 3,802,417 (electronic breathing activity detection system); and Russian abstract SU1069814A (artificial respiration apparatus including a thoracic cuff and solenoid operated back massage device.

There is a need for a reliable and portable respirator apparatus for improving a patient's breathing function when such functions are impaired as a result, for example, of an asthma attack and for restoring the breathing functions in extreme situations, for example, as a result of an accident.

SUMMARY OF THE INVENTION

A resuscitation breathing apparatus for aiding a patients breathing in accordance with the invention includes a high pressure source of breathable gas i.e., oxygen or a gas containing oxygen, and a inhalation chamber having an inlet and an outlet. An endotracheal adapter means, preferably in the form of a face mask for providing fluid communication to the patient's lungs, is connected to the outlet of the inhalation chamber. The face mask includes an inhalation check valve for allowing gas from the inhalation chamber to enter the patient's lungs and an exhalation check valve for venting the patient's exhaled gas. A inhalation valve is connected between the inlet of the inhalation chamber and the high pressure source. An inhalation valve control means responsive to the pressure in the inhalation chamber opens and closes the inhalation valve when the pressure reaches first and second predetermined values, respectively. An inhalation chamber venting means is connected to the inhalation chamber for venting gas therein and lowering the pressure within the chamber when the inhalation valve is in the closed position.

The apparatus preferably further includes chest compressing means for applying pressure to the patient's lungs during the exhalation phase i.e., when the inhalation valve is in the closed position to provide "active expiration". The chest compressing means comprises an inflatable cuff adapted to extend over the patient's chest and/or upper abdomen for applying pressure to the patient's lungs when inflated and a cuff inflation chamber having an inlet and an outlet with the outlet being connected to the cuff. A cuff inflation valve is connected between the inlet of the cuff inflation chamber and the high pressure source. A cuff inflation valve control means is responsive to the position of the inhalation valve for closing and opening the cuff inflation valve when the inhalation valve is in the open and closed positions, respectively. A cuff inflation chamber venting means is provided to lower the pressure within the cuff inflation chamber when the cuff inflation valve is in the closed position.

The features of the present invention may best be understood in reference to the following descriptions taken in conjunction with the accompanying drawings wherein like components are given the same reference numerals.

DESCRIPTION OF THE PREFERRED EMBODIMENT

Figure 1B:
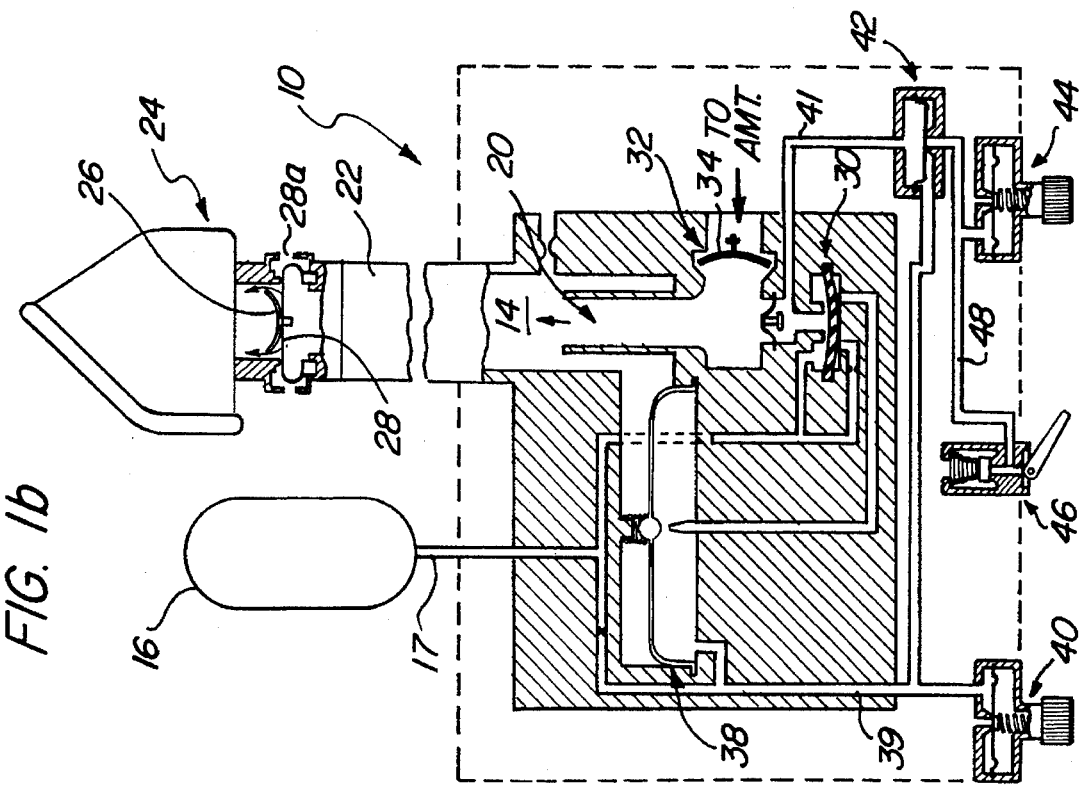
FIG. 1b is a schematic view of the apparatus of FIG. 1a configured to operate in the inhalation mode.
Figure 1A:
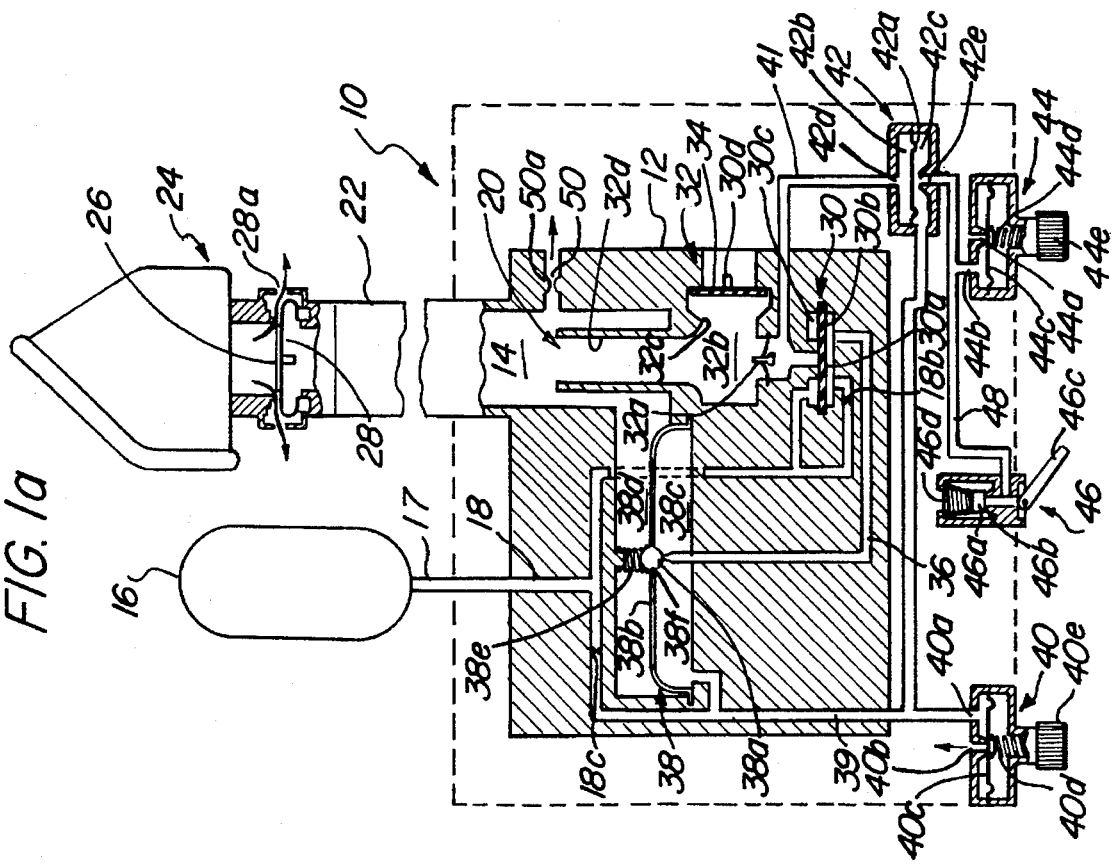
FIG. 1a is a schematic view of a resuscitation breathing apparatus in accordance with the invention with the inhalation chamber and associated valves shown in cross section and with the apparatus configured to operate in the exhalation mode.
Figure 2:
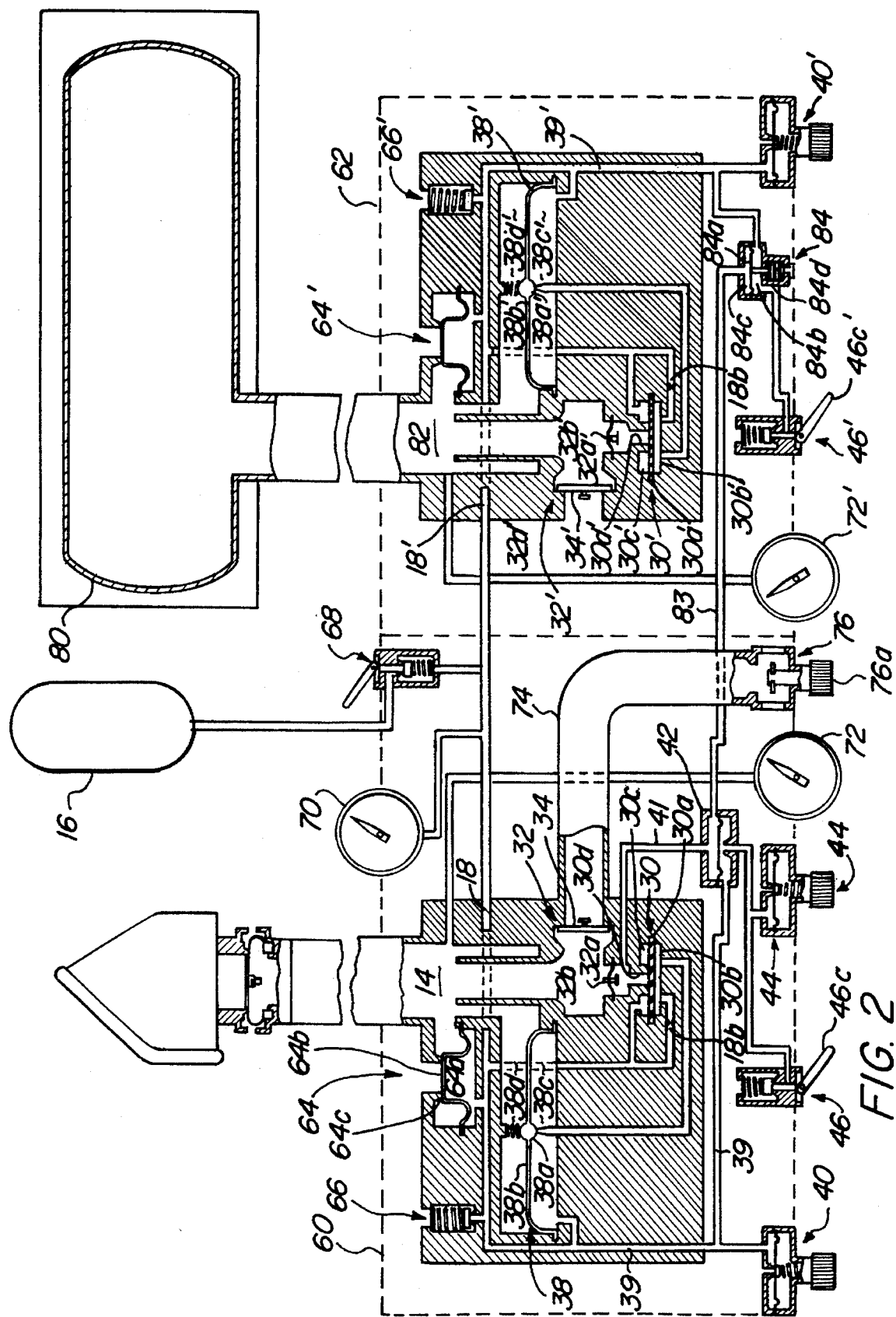
FIG. 2 is a schematic view of another embodiment of the invention including a pneumatic inflatable cuff for applying pressure to the chest and/or upper abdomen to force air out of a patient's lungs.

Referring now to FIGS. 1 and 2, a breathable gas dispenser 10 for automatically aiding a patient's breathing functions includes a pneumatic block or body member 12 defining an inhalation chamber or compartment 14. A high pressure source 16 of breathable gas, such as oxygen or gas containing oxygen, is connected to an inlet 17 of a high pressure line 18 in the block 12. The inhalation chamber 14 has an inlet 20 and an outlet 22. An endotracheal adapter in the form of a face mask 24 (for providing fluid communication to a patient's lungs) is connected to the outlet of the inhalation chamber 14 as is illustrated. The face mask includes an inhalation check valve 26 (shown in the closed and open positions in FIGS. 1a and 1b respectively) for allowing gas to enter the patient's lungs. The face mask also includes an exhalation check valve 28 for venting the patient's exhaled gas to atmosphere, through ports 28a.

An inhalation diaphragm valve 30 (first diaphragm valve) controls the flow of the respiration gas into the inhalation chamber. The valve 30 includes a flexible diaphragm 30a, a lower chamber 30b, and an upper chamber 30c, with a discharge port or outlet 30d. As is illustrated, both the upper and lower chambers are connected to the high pressure line 18 with a restricted orifice 18b in the portion of the high pressure line leading to the lower chamber. An eductor 32 connects the discharge port 30d of the inhalation valve 30 to the inhalation chamber. The eductor comprises a nozzle 32a, an expansion chamber 32b, (within which a lower or subatmospheric pressure is created) an intake port 32c (which connects the expansion chamber with atmosphere through a check valve 34) and a mixing chamber 32d wherein the respiration gas from the high pressure line 18 mixes with air drawn in from the atmosphere through check valve 34.

The lower chamber 30b of the inhalation valve is also connected, via a pressure relief line 36, to a discharge orifice 38a of a second diaphragm or membrane valve 38. The valve 38 includes a diaphragm or membrane 38b, a lower chamber 38c connected to the high pressure line 18 through a restricted orifice 18c and an upper chamber 38d which is in fluid communication with the inhalation chamber 14 as is illustrated. A spring 38e normally biases the membrane and its centrally disposed valve member 38f against the seat surrounding the orifice 38a. The lower chamber 38c of the valve 38 is also connected to an inlet 40a of a third diaphragm valve 40 via a pressure control line 39.

The valve 40 includes an outlet port 40b connected to the atmosphere, a diaphragm 40c, a spring 40d and a manually rotatable adjusting knob 40e for allowing an operator to adjust the force applied by the spring against the diaphragm 40c. The adjustable valve 40 sets the maximum allowable pressure in chamber 38c during the inhalation phase and accordingly controls the maximum inhalation chamber pressure (e.g., within the range of 1" to 12" Hg) as will become apparent.

A fourth diaphragm valve 42 includes a diaphragm 42a, an upper chamber 42b, a lower chamber 42c, an inlet port 42d (connected to the pressure control line 39) and an outlet port 42e. The upper chamber 42b is connected to the outlet 30d of the inhalation valve so that when the inhalation valve 30d is open the valve 42 is closed (i.e., diaphragm 42a closes the outlet port 42e) and visa versa as will be explained in more detail.

A fifth diaphragm valve 44 (similar in construction to valve 40) has an inlet 44a, an outlet 44b, a diaphragm 44c, a compression spring 44d and a rotatable adjustment knob 44e.

The position of the adjustment knob 44e sets the maximum allowable pressure on the underside of the diaphragm 44c and thereby controls the maximum pressure within chamber 14 during the exhalation or expiration phase provided that the inlet port 44b is not connected to atmosphere via a forced ventilation regime switch over valve 46 to be explained.

The regime switch over valve 46 includes a cylindrical valve member 46a which is seated against a valve seat 46b in the closed position as is shown in FIG. 1. A lever 46c when rotated clockwise moves the valve member upwardly against a compression spring 44d and opens the valve to connect the inlet port 44b of the valve 44 to atmosphere via line 48.

A vent line 50 and restricted orifice 50a connect the inhalation chamber to atmosphere to allow the pressure within the inhalation chamber to fall during the exhalation mode as will be discussed in more detail.

The apparatus of FIGS. 1a and 1b is designed to aid a patient's breathing with passive expiration (i.e., without applying pressure to the lungs during exhalation). To prepare the apparatus for operation the pressure control line 41 is initially connected to atmosphere (i.e., ambient pressure) through the forced ventilation regime switch over valve 46 (i.e., lever 46c is rotated counter clockwise). The high pressure respiration gas from source 16 (e.g., at 45 to 50 psi) flows in the high pressure line 18 (via a high pressure gas valve not shown in FIGS. 1a and 1b) into the upper chamber 30c and the lower chamber 30b of the inhalation valve (via restricted orifice 18b). Since the spring loaded diaphragm 38b of the valve 38 closes the outlet orifice of the line 36 the high pressure within the lower chamber 30b (due to the difference in the areas of the diaphragm 30a exposed to the upper and lower chamber pressure) maintains the inhalation valve 30 closed.

Gas flow through the inhalation valve 30 is thus prevented at this time. However, a small amount of gas (i.e., functional leakage) continues to flow through the restricted orifices 18c and 50a and the associated lines 41, 50, and valves (42g and 46 with respect to orifice 18c) to atmosphere. The apparatus is now ready for operation.

The mask 24 may now be placed over the patient's face, if not already in place. At the start of the inhalation phase, the patient creates, within the mask, a pressure slightly below the atmospheric pressure, for example, within the range of 0.5 to 0.8 centimeters of $H_2O$, which acts as the triggering event and opens the inhalation check valve 26. The sub-atmospheric pressure spreads into the inhalation chamber 14 and the upper chamber 38d of the second diaphragm valve 38. The differential pressure across the diaphragm 38b overcomes the resistance of spring 38e thereby opening the valve 38. This action connects the lower chamber 30b of the inhalation valve 30 to atmosphere via lines 36, 39 and valves 42, 44, and 46 thereby dumping the pressure within the lower chamber 30b of the inhalation valve 30. The high pressure gas in the upper chamber 30c of this valve now moves the diaphragm 30a downwardly and opens the inhalation valve 30 as is illustrated in FIG. 1b.

The gas from source 16 then flows through the outlet of the valve 30 via line 41 into the upper chamber 42b of the fourth diaphragm valve 42 forcing the diaphragm 42a against its seat, thereby closing the outlet port 42e and disconnecting the pressure line 39 from atmosphere. This action allows the pressure in chamber 38c to build up to a pressure determined by the setting of adjustment knob 40e of valve 40 (i.e., maximum inhalation pressure).

The positive pressure build up in the chamber 38c moves the diaphragm 38b even further from its seat, assuring a full dumping of the pressure in chamber 30b of the inhalation valve 30.

The gas flowing through the eductor nozzle 32a creates a low pressure in chamber 32b which opens check valve 34 and draws air from the atmosphere into the gas stream. The air and gas after mixing in chamber 32d flows into the inhalation chamber 14 and the patient's lungs through the inhalation check valve 26. It should be noted that the pressure in the outlet 30d of the inhalation valve when open (e.g., 5 to 10 psi) is considerably higher than the pressure in the inhalation chamber. This pressure is used to control the deflation of a pneumatic cuff of a chest compressor unit to be described in conjunction with FIG. 2.

The rising pressure in the inhalation chamber 14 closes the exhalation check valve 22 and cuts off the inhalation chamber (or breathing line) from atmosphere except for the small amount of leakage through the restricted orifice 50a and high pressure vent line 50. The pressure in the chamber 14 and in the patient's lungs continues to rise until it is about equal to the pressure in the lower chamber 38c of the valve 38 at which time the diaphragm 38b, under the pressure of spring 38c, will span the seat of valve 38 and close off the orifice in line 36 allowing excess pressure to build up in the lower chamber of valve 30 via restricted orifice 18b and high pressure line 18, which in turn closes the inhalation valve 30 and cuts off any further supply of breathing air. This action terminates the inhalation phase.

During the inhalation phase, the eductor 32 and the other valves of the apparatus assure an adequate supply of breathable gas in accordance with the needs of the patient while smoothly creating the maximum value of positive pressure in the lungs (and inhalation chamber) at the end of the inhalation phase. This maximum value which may be set by the attending physician or other operator, is determined by the setting of valve 40.

It should be noted that the use of the eductor 32 and atmospheric check valve 34 may be dispensed with where the source 16 is to be the sole source of breathable gas for the patient's lungs. In this event a check valve or other pressure reduction means may be used in view of the eductor to ensure the proper operation of valve 42.

The exhalation phase commences as soon as the inhalation valve 30 is closed, thereby decreasing the pressure in the outlet 30c and opening the valve 42. This action reconnects the pressure control line 39 to atmosphere and drops the pressure in chamber 38c of the valve 38. Air within the inhalation chamber and in the upper chamber 38d of the valve 38 is vented to atmosphere through the vent line 50 and restricted orifice 50a to lower the pressure within the inhalation chamber 14. The exhalation check valve 28 now opens, allowing the patient to exhale the expired gas to atmosphere and dump the positive pressure in the lungs as is illustrated in FIG. 1a.

During this exhalation phase, the inhalation check valve 26 in the face mask remains closed due to the differential pressure thereon, thereby assuring a minimum "dead" space for the expired gas and a minimum content of carbon dioxide gas in the gas mixture to be inhaled during the subsequent inhalation phase.

Referring now to FIG. 2, there is illustrated a combined breathable gas dispenser 60 and chest (and/or upper abdomen) compressor 62. The gas dispenser 60 is identical to the one shown in FIGS. 1a and 1b except for several additional components and one substituted component. An exhalation diaphragm dump valve 64 (sixth diaphragm valve) is substituted for the vent line 50 and restricted orifice 50a to reduce the pressure in the inhalation chamber during the exhalation mode. An added pressure relief safety valve 66 is connected between atmosphere and the pressure control line 39 to limit the maximum pressure build-up in the pressure control line and thus, control the maximum inhalation pressure independently of the setting of valve 40.

A high pressure gas valve 68 (similar to valve 46) is provided to connect the high pressure line 18 to the aspiration gas source 16. A pair of pressure gauges (e.g., manometers) 70 and 72 are connected to the high pressure line 18 and the inhalation chamber 14, respectively, to allow a physician or operator to monitor the pressure at source 16 and to monitor and adjust the maximum inhalation pressure (via knob 40e). In addition, an air intake conduit 74 is connected between the atmosphere check valve 34 and an air adjustment valve 76 to allow a physician or other operator to adjust, via control knob 76a, the quantity of air flowing into the eductor 32 and thereby control the ratio of the aspiration gas from source 16 (which may be pure oxygen) to air which is supplied to the patient's lungs.

The inhalation dump valve 64 has a lower chamber 64a in fluid communication with the pressure control line 39 and a diaphragm 64b which is pressed against an annular seat 64c in the closed position and is moved downwardly from the seat in the open position to connect the inhalation chamber to atmosphere. The dump valve 64 closes at the initiation of the inhalation phase as a result of the increase in pressure in the pressure control line 39 and opens at the beginning of the exhalation phase to dump the pressure in the inhalation chamber as a result of the falling pressure in line 39.

Most of the components of the chest compressor 62 correspond to components in the gas dispenser 60 and are given the same reference numerals primed as is illustrated. It should be noted that valve 40' controls the maximum cuff inflation pressure (via adjustment knob 40e') in the same manner that valve 40 controls the maximum inflation chamber pressure. Safety valve 66' like valve 66, limits the maximum cuff inflation pressure. Manometer 72' provides a measurement of the cuff inflation pressure. The dump valve 64' also functions like valve 64 to lower the pressure within the cuff inflation chamber during the inhalation phase.

The chest compressor 62 includes, in addition to components marked with prime reference numerals, a pneumatic cuff 80 adapted to be placed around the patient's chest and/or upper abdomen, a cuff inflation chamber 82 connected between the eductor 32' and the pneumatic cuff 80, and an inhalation valve outlet pressure sensing valve 84. The valve 84 includes a diaphragm 84a, a lower chamber 84b connecting the pressure control line 39' to the valve 46', an upper chamber 84c connected to the outlet 32d of the inhalation valve via lines 41 and 83 and a spring biased valve member 84d. When the diaphragm 84a is depressed (as a result of the high pressure gas from the outlet of the inhalation valve 30) the valve member 84d connects the lower chamber 84b and the pressure control line 39' to atmosphere The valves 30' 38', 40', 84' and 64' are some times hereinafter referred to as the seventh, eighth, ninth, tenth and eleventh diaphragm valves, respectively.

The apparatus of FIG. 2 is arranged to aid a patient's breathing with active expiration (i.e., applying pressure to the chest and/or upper abdomen during exhalation). It should be noted that when the handle 46c' of the valve 46' is rotated clockwise, the pressure control line 39' is permanently connected to atmosphere, thereby disabling the chest compressor 62 so that the apparatus will function in the aided breathing/passive expiration regime only as was described with respect to FIGS. 1 and 2.

To operate the apparatus of FIG. 2 in the active expiration regime the handle 46c' of the valve 46' is rotated to the position shown to disconnect the pressure control line 39' from atmosphere. As a result when the inhalation valve 30 closes, at the termination of the inhalation mode, the pressure at the outlet of the inhalation valve and in the pressure sensing line 83 drops. This action causes the diaphragm 84a of the valve 84 to move upwardly allowing the valve member 84d to engage its cooperating valve seat and disconnect the cuff pressure control line 39' from atmosphere. As a result the pressure in line 39' and in the lower chamber 38c' decreases causing valve 38' to open thereby venting gas from the lower chamber 30b' of the exhalation valve 30' and opening valve 30'. The rising pressure in the pressure control line 39' also closes the dump valve 64' allowing gas from the source 16 and air from the atmosphere (via check valve 34' an eductor 32) to inflate the cuff 80 through the cuff inflation chamber 82 in a manner similar to that described with respect to the apparatus of FIGS. 1a and 1b. The cuff 80 depresses the chest and/or upper abdomen to force air out of the patient's lungs.

When the inhalation valve 32 opens the pressure in line 82 and in the upper chamber 84c of the valve 84 rises opening valve 84 and to vent the pressure control line 39' to atmosphere. This action closes valves 38' and 30' and opens dump valve 64' thereby deflating the cuff 80.

Figure 3A:
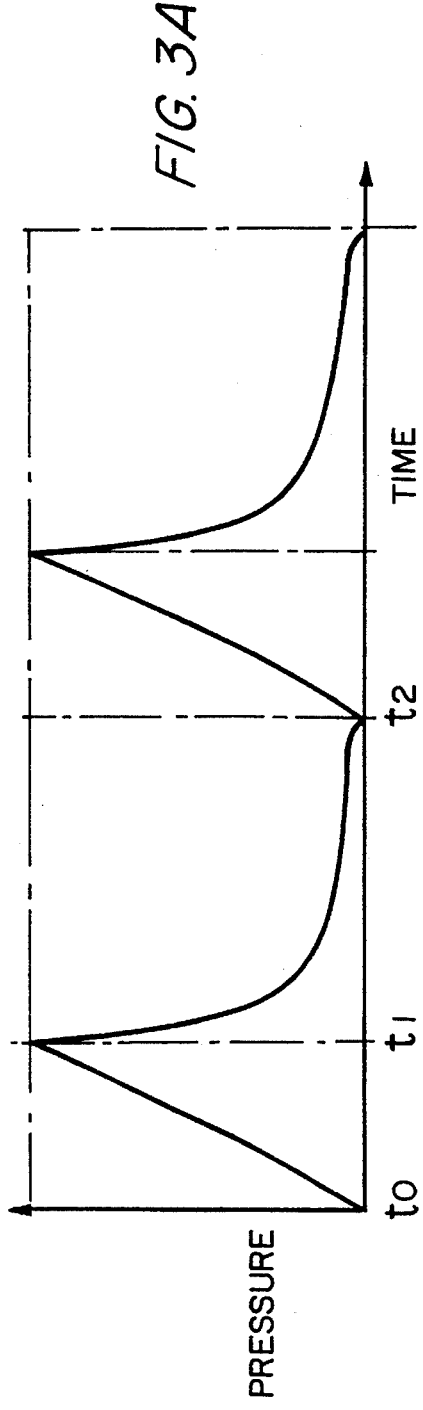
FIG. 3A is a graph showing the pressure profile in the inhalation chamber of the apparatus of FIG. 2.
Figure 3B:
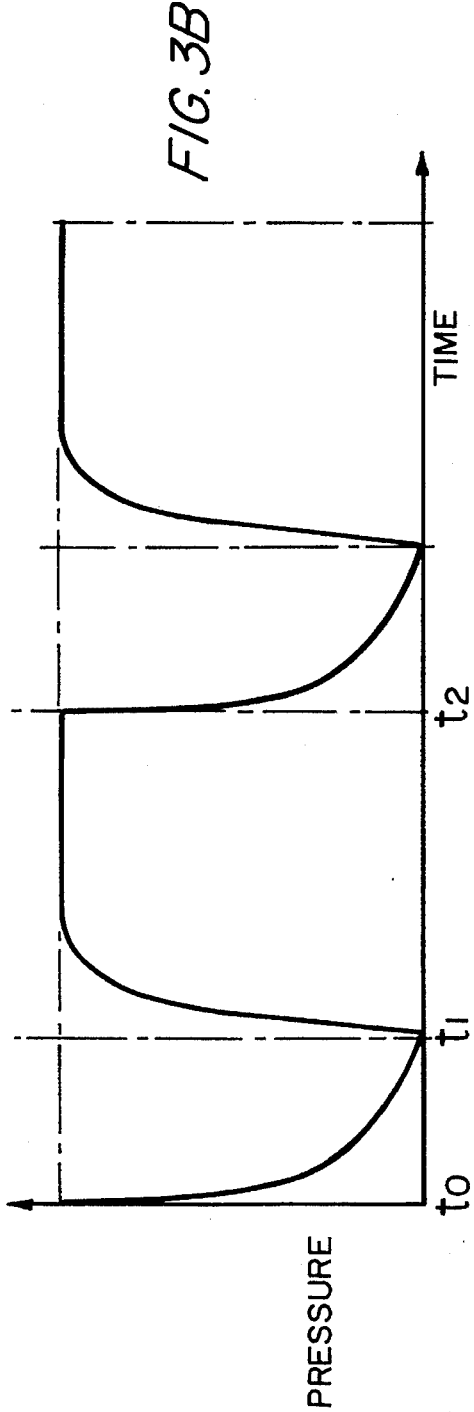
FIG. 3B is a graph showing the pressure profile in the cuff inflation chamber.

Referring now to FIGS. 3A and 3B, there is illustrated the pressure changes in the inflation chamber 14 (and the patient's lungs) and in the pneumatic cuff 80 when the apparatus of FIG. 2 is operating in the aided breathing and active expiration regime. The graph of FIG. 3A represents the pressure changes in the inhalation chamber 14 while the graph of FIG. 3B represents the pressure changes in the pneumatic cuff 82. The ratio of the inhalation time, (i.e., $t_0$ to $t_1$), to exhalation time ($t_1$ to $t_2$) is established by the patient's natural breathing cycle. The build up of positive pressure in the pneumatic cuff occurs in synchronization with the decrease in the positive pressure in the inhalation chamber or lungs, and visa versa. Such pressure changes are 180° out of phase with each other as is illustrated in FIGS. 3A and 3B.

The apparatus of FIG. 2 is also designed to be operated in an artificial respiration regime, that is, where the breathing cycle or frequency is determined by the apparatus (as set by the physician or operator) when the patient is unable to initiate the inhalation phase. To operate in this manner, the lever 46c of the valve 46 in the gas dispensing unit 60 is rotated to the position shown in FIG. 2 to close off the free dumping of the functional leakage from the pressure control line 39 during exhalation. As a result at the initial moment of the inhalation phase a small (trigger) excess pressure occurs in the pressure control line 39 as a result of the resistance of the valve 44 to the functional leakage. This small increase in pressure opens the valve 38 and the inhalation and subsequent exhalation phases proceed in a manner analogous to the aided breathing/active expiration regime discussed previously with respect to FIG. 2. The breathing cycle or frequency can be set in this regime by means of valve 40. In this mode, valve 44 controls the minimum pressure in the inhalation chamber 14. Thus, in the artificial respiration regime, an overpressure (i.e., above ambient) may be maintained in the inhalation chamber and in the patient's lungs.

This artificial respiration regime will continue until the breathing functions of the patient resume. When the patient resumes breathing, the apparatus will switch automatically from the artificial regime to the aided breathing/active expiration regime in which the creation of a small subatmospheric pressure in the inhalation chamber opens valve 38. The apparatus will also switch back to the artificial regime when the patient's breathing function is disturbed again. It should be noted that the apparatus of FIGS. 1a and 1b (without the chest compressor 62 of FIG. 2) can also be operated in the artificial respiration regime.

There has thus been described a novel and automatic resuscitation breathing apparatus which can be operated to force ventilate a patient's lungs in an aided breathing regime with passive or active expiration in which the patient controls the breathing frequency or in an artificial breathing regime in which the apparatus controls the breathing frequency. The apparatus may be used for long periods of time without subjecting the patient to undue risk. Various modifications and additions to the disclosed embodiments will become apparent to those skilled in the art without departing from the scope of the invention as defined in the appended claims. For example, a separate pressurized gas source may be used to inflate the pneumatic cuff 80.

What is claimed is:

1. Resuscitation breathing apparatus for improving a user's breathing comprising:

a) a high pressure source of breathable gas;

b) an inhalation chamber having an inlet and an outlet;

c) endotracheal adapter means for connection to the patient's airway to provide fluid communication to the lungs, the airway means being connected to the outlet of the inhalation chamber and including an inhalation check valve for allowing gas from the inhalation chamber to enter the patient's lungs and an exhalation check valve for venting the patient's exhaled gas;

d) an inhalation valve connected between the inlet of the inhalation chamber and the high pressure source, the inhalation valve comprising a first diaphragm valve with first and second pressure actuating chambers disposed on opposite sides of the diaphragm, the diaphragm having a greater area exposed to the second chamber than the first chamber, whereby the valve is in a closed position when the pressure in the second chamber exceeds the pressure in the first chamber by a preset value and in an open position when the pressure in the second chamber falls below the preset value;

e) inhalation valve control means responsive to the pressure in the inhalation chamber to open and close the inhalation valve when the pressure reaches first and second predetermined pressures, respectively, the inhalation valve control means including means for connecting the first and second chambers to the pressurized source with a restrictor for limiting the flow rate of gas to the second chamber and a second diaphragm valve with first and second chambers and a spring means for biasing the diaphragm of the second valve toward a closed position, the second diaphragm valve being arranged to vent the second chamber of the first diaphragm valve when in the open position and to prevent gas from escaping from the second chamber when in the closed position;

f) the inhalation valve control means further including means for connecting the first chamber of the second diaphragm valve to the inhalation chamber, means for connecting the second chamber of the second diaphragm valve to the pressurized source and means responsive to the closed position of the inhalation valve for venting the gas within the second chamber of the second diaphragm valve whereby the second diaphragm valve will remain closed as the pressure within the inhalation chamber decreases from the second predetermined pressure; and g) inhalation chamber venting means for venting gas within the inhalation chamber to lower the pressure therein from the second predetermined pressure when the inhalation valve is in the closed position.

2. The invention of claim 1 wherein the means for connecting the second chamber of the second diaphragm valve to the pressurized source includes a restrictor for limiting the flow rate of gas to the second chamber thereof.

3. The invention of claim 2 further including maximum inhalation pressure control means for adjusting the magnitude of the first predetermined pressure.

4. The invention of claim 3 further including maximum exhalation pressure control means for adjusting the magnitude of the second predetermined pressure.

5. The invention of claim 4 wherein the first predetermined pressure is within the range of about 3" to 12" of water.

6. The invention of claim 5 wherein the second predetermined pressure is within the range of about 0" to 1" of water.

7. The invention of claim 6 wherein the maximum inhalation pressure control means comprises a third diaphragm valve connected between the second chamber of the second diaphragm valve and atmosphere and means for adjusting the pressure required to open said third diaphragm valve to connect the second chamber of the second diaphragm valve to atmosphere.

8. The invention of claim 7 wherein the inhalation valve has an outlet through which gas flows to the inhalation chamber and wherein the means for venting the gas within the second chamber of the second diaphragm valve includes a fourth diaphragm valve responsive to the gas pressure in the outlet of the inhalation valve whereby gas is vented from said second chamber of the second diaphragm valve through the fourth valve only when the inhalation valve is closed.

9. The invention of claim 8 wherein the fourth diaphragm valve has an inlet connected to the second chamber of the second diaphragm valve and an outlet through which gas is vented and further including a fifth diaphragm valve and an on/off valve connected to the outlet of the fourth diaphragm valve, the on/off valve being arranged to connect the outlet of the fourth valve to atmosphere when open, the fifth diaphragm valve being arranged to connect the outlet of the fourth diaphragm valve to atmosphere when open including means for adjusting the pressure required to open said fifth valve whereby the breathing apparatus will operate in the artificial respiration regime when the on/off valve is closed, the breathing frequency being dependent upon the pressure required to open the third diaphragm valve.

10. The invention of claim 1 wherein the inhalation valve has an outlet and further including first eductor means connected in series with the outlet of the inhalation valve, the first eductor having a low pressure chamber disposed between the inlet and outlet for entraining gas into the high pressure gas flowing through the outlet of the inhalation valve and means for connecting the low pressure chamber of the first eductor means to atmosphere.

11. The invention of claim 10 wherein the means for connecting the first eductor to atmosphere includes means for adjusting the volume of the entrained air.

12. The invention of claim 1 wherein the means for connecting the first eductor to atmosphere includes a check valve to isolate the low pressure chamber from atmosphere when the pressure therein is above atmospheric pressure.

13. The invention of claim 1 wherein the means for venting gas within the inhalation chamber comprises an exhalation select valve responsive to the closed position of the exhalation valve for venting the gas within the inhalation chamber.

14. The invention of claim 13 wherein the exhalation relief valve is a sixth diaphragm valve connected between the inhalation chamber and atmosphere and responsive to the pressure within the second chamber of the second diaphragm valve for venting the gas within the inhalation chamber to atmosphere when the inhalation valve is in the closed position.

15. Resuscitation breathing apparatus for improving a user's breathing comprising:

a) a high pressure source of breathable gas;

b) an inhalation chamber having an inlet and an outlet;

c) endotracheal adapter means for connection to the patient's airway to provide fluid communication to the lungs, the airway means being connected to the outlet of the inhalation chamber and including an inhalation check valve for allowing gas from the inhalation chamber to enter the patient's lungs and an exhalation check valve for venting the patient's exhaled gas;

d) an inhalation valve connected between the inlet of the inhalation chamber and the high pressure source;

e) inhalation valve control means responsive to the pressure in the inhalation chamber to open and close the inhalation valve when the pressure reaches first and second predetermined pressures, respectively;

f) inhalation chamber venting means for venting gas within the inhalation chamber to lower the pressure therein from the second predetermined pressure when the inhalation valve is in the closed position;

g) chest compressing means including an inflatable cuff adapted to extend over the patient's chest and/or upper abdomen for compressing the patient's chest when inflated;

h) a cuff inflation chamber having an inlet and an outlet, the outlet being connected to the cuff;

i) a cuff inflation valve connected between the inlet of the cuff inflation chamber and a high pressure gas source;

j) cuff inflation valve control means responsive to the position of the inhalation valve to close and open the cuff inflation valve when the inhalation valve is open and closed, respectively; and k) cuff inflation chamber venting means for venting gas within the cuff to lower the pressure therein when the cuff inflation valve is in the closed position; and i) the cuff inflation valve comprising a seventh diaphragm valve with first and second pressure actuating chambers disposed on opposite sides of the diaphragm the diaphragm, the diaphragm of the seventh valve having a greater area exposed to the second chamber than the first chamber, whereby the seventh valve is in a closed position when the pressure in the second chamber exceeds the pressure in the first chamber by a preset amount and in an open position when the pressure in the second chamber falls below the preset valve and the cuff inflation valve control means includes means for connecting the first and second chambers to the pressurized source and an eight diaphragm valve with first and second chambers for selectively venting gas from the second chamber of the cuff inflation valve to reduce the pressure therein and allow the gas pressure within the first chamber of the cuff inflation valve to open said valve and inflate the cuff.

16. The invention of claim 15 wherein the means for connecting the second chamber of the cuff inflation valve to the pressurized source includes a restrictor for limiting the flow rate of the gas to the second chamber.

17. The invention of claim 16 wherein:

the eighth diaphragm valve includes a spring means for biasing the diaphragm toward a closed position, the eighth diaphragm valve being arranged to vent the second chamber of the seventh diaphragm valve when in the open position and to prevent gas from escaping from the second chamber when in the closed position; and the cuff inflation valve control means further includes means for connecting the first chamber of the eighth diaphragm valve to the cuff inflation chamber, means for connecting the second chamber of the eighth diaphragm valve to the pressurized source and means responsive to the closed position of the cuff inflation valve for venting the gas within the second chamber of the eighth diaphragm valve whereby the eighth diaphragm valve will remain closed as the pressure within the cuff inflation chamber decreases.

18. The invention of claim 17 wherein the means for connecting the second chamber of the eighth diaphragm valve to the pressurized source includes a restrictor for limiting the flow rate of gas to the second chamber thereof.

19. The invention of claim 18 further including maximum inhalation pressure control means for adjusting the magnitude of the first predetermined pressure.

20. The invention of claim 19 wherein the maximum cuff inflation pressure control means comprises a ninth diaphragm valve connected between the second chamber of the eighth diaphragm valve and atmosphere and means for adjusting the pressure required to open said ninth diaphragm valve to connect the second chamber of the eighth diaphragm valve to atmosphere.

21. The invention of claim 20 wherein the cuff inflation valve has an outlet through which gas flows to the inhalation chamber and wherein the means for venting the gas within the second chamber of the eighth diaphragm valve includes a tenth diaphragm valve responsive to the gas pressure in the outlet of the inhalation valve whereby gas is vented from said second chamber of the eighth diaphragm valve through the tenth valve only when the inhalation valve is open.

22. The invention of claim 21 wherein the tenth diaphragm valve has an inlet connected to the second chamber of the eighth diaphragm valve and an outlet through which gas is vented to the atmosphere.

* * * * *

UNITED STATES PATENT AND TRADEMARK OFFICE
CERTIFICATE OF CORRECTION

PATENT NO. : 5,492,115

DATED : February 20, 1996

INVENTOR(S) : Abramov et al

It is certified that error appears in the above-identified patent and that said Letters Patent is hereby corrected as shown below:

Column 8, line 57, "out let" should read --outlet--.

Column 10, line 28, "claim 1" should read --claim 11--.

Signed and Sealed this

Thirtieth Day of July, 1996

Attest:

BRUCE LEHMAN

*Attesting Officer*

*Commissioner of Patents and Trademarks*